United States Patent [19]

Farona et al.

[11] 3,984,483
[45] Oct. 5, 1976

[54] METHOD FOR REACTING ORGANIC HALIDES

[75] Inventors: Michael F. Farona, Cuyahoga Falls; James F. White, Akron, both of Ohio

[73] Assignee: The University of Akron, Akron, Ohio

[22] Filed: Apr. 10, 1974

[21] Appl. No.: 459,483

Related U.S. Application Data

[60] Division of Ser. No. 339,637, March 9, 1973, Pat. No. 3,832,403, which is a continuation-in-part of Ser. No. 119,908, March 1, 1971, abandoned.

[52] U.S. Cl........................... 260/623 H; 260/543 R; 260/612 R; 260/612 D; 260/613 D; 260/613 R; 260/619 R; 260/620; 260/650 R; 260/649 R

[51] Int. Cl.$^2$.......................................... C07C 37/00

[58] Field of Search........ 260/612 D, 613 R, 613 D, 260/619 R, 621 R, 624 C, 625, 623 H

[56] References Cited
UNITED STATES PATENTS

3,832,403  8/1974  Farona et al.................... 260/619 R

OTHER PUBLICATIONS

Farona et al., "J. Am. Chem. Soc.", vol. 93, pp. 2826–2827 (1971).

*Primary Examiner*—Norman Morgenstern
*Attorney, Agent, or Firm*—Hamilton, Renner & Kenner

[57] ABSTRACT

A method for carrying out reactions of the Friedel-Crafts type, such as alkylation, acylation, polymerization, sulfonylation and dehydrohalogenation. The reactions are catalyzed by arene-metal tricarbonyl complexes and when the reaction vessel contains aromatic substrates the catalyst may be generated in situ from a metallic hexacarbonyl. The arene-metal tricarbonyl catalyst is more selective than conventionally employed Friedel-Craft catalysts in that it yields generally para isomers with little of the ortho variety and very little if any of the meta variety when the aromatic substrate is reacted with organic halide. It is also possible to form the arene-metal tricarbonyl catalyst outside of the reaction vessel and then proceed by adding it to the vessel containing the substrate and the organic halide as is the case with dehydrohalogenation reactions wherein there are no aromatic rings available, the substrate in that instance being aliphatic.

9 Claims, No Drawings

METHOD FOR REACTING ORGANIC HALIDES

CROSS REFERENCE TO RELATED APPLICATION

This application is a divisional application of U.S. Ser. No. 339,637, now U.S. Pat. No. 3,832,403 which is in turn a continuation-in-part application of U.S. Ser. No. 119,908, filed Mar. 1, 1971, now abandoned.

BACKGROUND OF THE INVENTION

Substitution of halogens from organic compounds by other organic groups or the mere removal of halogens, without substitution, to form new organic compounds is well known by a variety of standard name reactions. The Friedel-Crafts type of reactions, usually carried out by the catalyst aluminum trichloride, are an example.

The reactivity of the arene-metal tricarbonyl complexes has also been examined and it is known that the tricarbonylchlorobenzenechromium complex will enter into a nucleophilic reaction with methyl alcohol to form the anisole complex. Further, electrophilic reactions are also facilitated such as Friedel-Crafts acetylation of the tricarbonyl-benzene chromium complex with acetyl chloride in the presence of aluminum trichloride. Both types of reaction yield a product which retains the arene-metal tricarbonyl complex.

SUMMARY OF THE INVENTION

It is therefore an object of the present invention to provide a method for reacting organic halides in alkylations acylations, polymerizations, sulfonylations and dehydrohalogenations.

It is another object of the present invention to provide a method for carrying out these reactions in the presence of an arene-metal tricarbonyl catalyst.

It is a further object of the present invention to employ a catalyst which is easier to use, with respect to storage and handling, in that the catalyst may be generated in solution within the reaction vessel or without the reaction vessel and subsequently added thereto.

It is yet another object of the present invention to employ a catalyst which promotes attack on the aromatic ring generally at the para position rather than at the ortho position and usually excludes attack at the meta position.

These and other objects of the invention, and the advantages thereof, will be apparent in view of the detailed disclosure of the invention as set forth below.

In general, it has now been found that an organic halide RX, and an arene-metal tricarbonyl represented by the general formula,

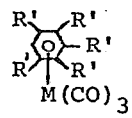   F(1)

will react to form a carbonium ion $R^+$.

It was further found that the highly reactive carbonium ion will release a hydrogen ion, or react in situ and in a repetitive process with the original organic halide or with other organic compounds present within the reaction vessel. Many different classes of products may be formed by predetermined selection of the appropriate organic reactants.

DESCRIPTION OF THE PREFERRED EMBODIMENTS

The catalyst may be prepared in advance of a catalysis reaction according to the reaction mechanism

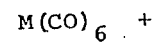

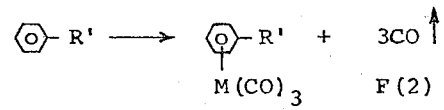   F(2)

where R' is selected from the class consisting of electron donating and ring activating groups such as hydrogen, alkyl groups having from 1 to about 6 carbon atoms, alkoxide groups having from 1 to about 4 carbon atoms, aryl and aryloxide groups having from 6 to about 12 carbon atoms including alkyl substituents, amino and hydroxide. The metal, M, is selected from the group consisting of Cr, Mo, and W with molybdenum being preferred.

Representative alkyl groups including methyl, ethyl, isopropyl, t-butyl, pentyl, hexamethyl and the like. Representative alkoxide groups include methoxy, ethoxy, propoxy, butoxy, sec-butoxy and the like. Representative aryl groups include phenyl, naphthyl and the phenyl ring with substituted alkyl groups such as methyl, ethyl, propyl, butyl, sec-butyl, pentyl, 2-pentyl, hexamethyl and the like. A representative aryloxide is diphenyl ether.

R' may further be selected from the class consisting of ring deactivating and electron withdrawing groups such as the halides, the haloalkyls, the alkylbenzoate esters, the aldehydes and sulfonyl halides, particularly sulfonyl chloride. Representative halides are fluoro, chloro and bromo, and representative alkylbenzoate esters are those having from 1 to 3 carbon atoms such as methyl benzoate, ethyl benzoate, propyl benzoate and isopropyl benzoate. Representative aldehydes are those having from 1 to 4 carbon atoms. Representative haloalkyl groups include methyl bromide, methyl chloride and methyl fluoride.

In addition to the aforementioned mono-substituted phenyl compounds which may be utilized it is also possible to select poly-substituted phenyl compounds having up to five substituent groups. The generic formula for such a compound may be expressed as follows:

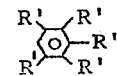   F(3)

wherein R' may be the same as any of the aforementioned R' groups including hydrogen. As will be obvious to one skilled in the art, a large number of the existing poly-substituted phenyl compounds can thus be used in accordance with the teaching of this pioneer invention. Since it would be impractical to provide an all inclusive listing, only some of the representative compounds according to formula F(3) will be set forth.

Representative compounds wherein one or more of the R' groups are other than hydrogen include anisole, chlorobenzene, benzyl chloride, benzyl fluoride, phenol, toluene, t-butyl benzene, o,m and p-dichlorobenzene, diphenyl ether, biphenyl, o,m and p-xylene, p-toluene sulfonyl chloride, methyl benzoate, ethyl benzoate, propyl benzoate, isopropyl benzoate, 2,3-dimethoxyaniline, 2,4-dihydroxytoluene, 3,4-dimethoxytoluene, 4-hydroxy-3-methoxytoluene, 1,2,4,5-tetramethylbenzene, 3,4,5-trihydroxytoluene and 1,3-dihydroxy-4,5,6-trimethylbenzene.

Selection of any specific aromatic compound will of course be dependent upon factors such as the product desired and the availability or existence of the compound. A person skilled in the art will generally know numerous existing compounds. Moreover, as to other compounds, any standard reference book, such as the CRC Handbook of Chemistry and Physics, could be consulted thus enabling the skilled artisan to obtain readily the names of other existing compounds.

Preparation of the catalyst according to F(2) is necessarily precedent to a catalysis reaction when phenyl radicals are neither present nor constituents of the reactants chosen to form the product compounds. Thus, in the case of dehydrohalogenation reactions, the catalyst will promote the formation of the olefin, but it must be prepared in advance as there are no aromatic rings available in the reaction vessel.

Thus, a utility of the present invention is that this catalyst may be generated during the catalysis reaction. Thus, when the metal hexacarbonyl and a substrate reactant having a phenyl radical constituent are brought together in a reaction vessel, the arene-metal tricarbonyl catalyst will be generated in situ. Upon the addition of the desired organic halide, the particular reaction, e.g., alkylation, acylation, polymerization, sulfonylation, will then proceed to form the desired products.

According to the method of the present invention, aromatic substrates are combined with organic halides, having the generic formula RX, in the reaction vessel. The catalyst removes the halogen forming a highly reactive carbonium ion on the organic moeity R. Subsequent attack by the carbonium ion upon the substrate molecule yields a product, resulting from the attachment of the organic radical R to the substrate, and a hydrogen ion. The hydrogen ion quickly removes the halogen with at least partial regeneration of the catalyst. In this manner alkylations, acylations, polymerizations and sulfonylations occur. Of course, the catalyst also promotes dehydrohalogenation. However, since there is no aromatic substrate the catalyst merely removes the halogen from the organic halide to yield an olefin.

The organic halide RX, wherein X is generally selected from bromine, chlorine and fluorine, will be chosen according to the desired reaction, e.g., alkyl, alkyl substituted phenyl or acyl halides for alkylation and acylation, sulfonyl halides for sulfonylation and polymerization and alkyl halides for dehydrohalogenation. The organo group, or R, may therefore be selected from the class consisting of alkyl radicals having from 1 to about 20 carbon atoms and alkyl substituted phenyl radicals having from 7 to about 12 carbon atoms. Alkoxide radicals having from 1 to about 4 carbon atoms and aldehydes having from 1 to about 4 carbon atoms, and haloalkyl groups such as methyl bromide, methyl chloride, and methyl fluoride may also be used in the copolymerization reaction. Substituted phenyl and naphthyl having the halogens attached to the alkyl substituents are preferred to phenyl radicals for the alkylation and polymerization reactions inasmuch as the catalyst removes, for instance, chlorine much more readily from benzyl chloride than from chlorobenzenes.

Representative alkyl groups include methyl, ethyl, propyl, butyl, pentyl, hexyl, heptyl, octyl, nonyl, decyl isomers thereof and the like. Representative substituted phenyl radicals include tolyl, xylyl, methyl naphthyl and the like. Furthermore, when selecting the xylenes, dihalo compounds may be utilized as the catalyst can readily remove both halogens from their methyl partner. As before, the skilled artisan can refer to a reference handbook to ascertain the existing organic halides which he may desired to react.

Whether the catalyst is prepared within the reaction vessel by reacting molybdenum hexacarbonyl with the aromatic substrate, or it is separately prepared and added, the reactants are all placed within the reaction vessel. Generally, the reactants are soluble within the substrate; however, if such is not the case, the reaction may be carried out in heptane or any other saturated liquid hydrocarbon or any aryl such as benzene or substituted benzene. The reaction is preferably carried out in an inert atmosphere such as nitrogen. In order to generally initiate the reaction, the vessel is usually fitted with a reflux condenser and heated from ambient temperatures through a temperature range of a few degrees to approximately 135° C, depending upon the type of reaction and the reactants. Reaction time is also dependent upon the latter factors and accordingly ranges from about one hour to about thirty six hours or longer. During this time it is necessary to keep the reactants mixed which may be readily accomplished with a conventional magnetic stirrer or the like. Mechanisms for the various reactions are as follows:

An alkylation according to the present invention is thought to proceed according to the following reaction mechanism;

Step 1

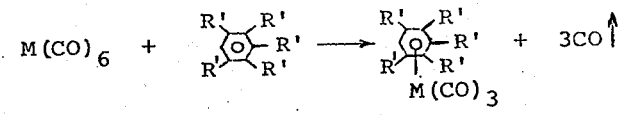

Step 2

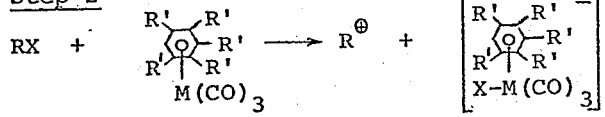

Step 3

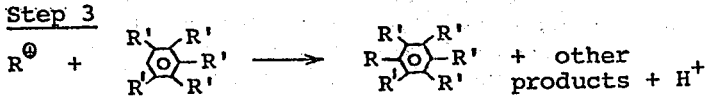

Step 4

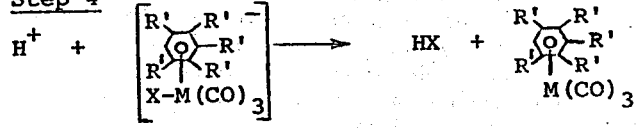

F(4)

where
R is an alkyl or alkyl substituted phenyl group as noted above
and R' is hydrogen, alkyl, alkoxide, sulfonyl chloride, hydroxide, aryl or aryl oxide as noted above
and M is a metal from the group, Cr, Mo and W,
and X is a halogen from the group of Br, Cl and F.

The catalyst is formed in the reaction vessel from part of the aromatic substrate reactant or it may be added in its active form whereby Step 1 is omitted. In Step 2, it proceeds to remove the halogen from the organic halide, RX, resulting in the formation of a highly reactive carbonium ion, $R^+$, which subsequently attacks the remaining part of the aromatic substrate, as in Step 3, with concurrent release of a hydrogen ion. In Step 4, the hydrogen ion removes the halogen and the catalyst is regenerated.

An acylation according to the present invention is thought to proceed according to the following reaction mechanism;

Step 1

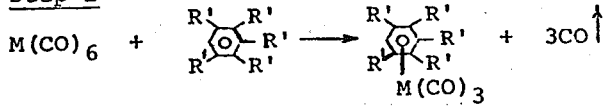

Step 2

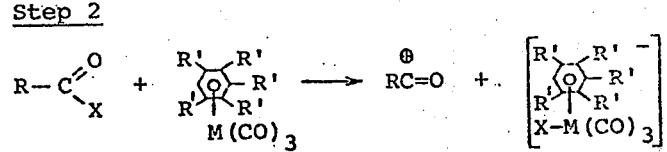

Step 3

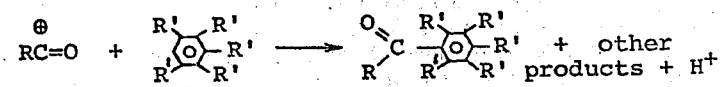

Step 4

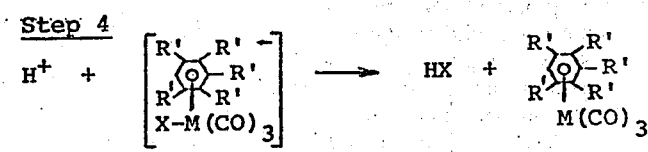

F(5)

where
R is an alkyl or alkyl substituted phenyl group as noted above and R' is hydrogen, alkyl, alkoxide or hydroxide, aryl or aryloxide as noted above
and M is a metal from the group Cr, Mo and W,
and X is a halogen from the group of Br, Cl and F.

The catalyst is again formed in Step 1, as described before or merely added directly to the reactants. In Step 2 it proceeds to remove the halogen from the organic acid halide resulting in the formation of a highly reactive acyl cation $RC^+=O$, which subsequently attacks the aromatic substrate reactant, as in Step 3, with concurrent release of a hydrogen ion. In Step 4, the hydrogen ion removes the halogen and the catalyst is regenerated.

Two types of polymers may be produced according to the present invention. A branched structure may be formed by the polymerization of one monomeric substance or the combination of two monomers. A linear polymer may be produced by selecting an aryl substrate, A, having only two positions subject to carbonium ion attack and having ligands at each of the other positions relatively unsusceptible to carbonium ion attack. The organic halide selected, B, is a dihalo-compound such that carbonium ions may form at two ends of the molecule, thus forming a linear polymerization of the type AB.

Polymerization to form a branched polymer according to the present invention is thought to proceed according to the following reaction mechanism;

Step 1

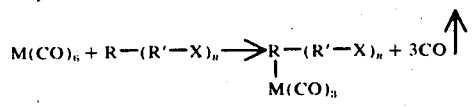

Step 2 where n = 1

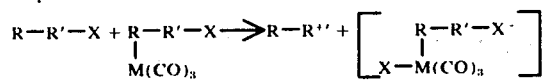

Step 3

Step 4

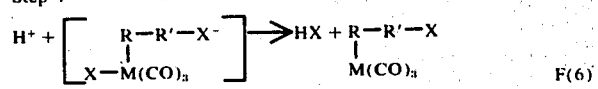

where
R is an aryl radical as noted above
and R' is alkyl, alkoxide, or haloalkyl as noted above,
and M is a metal from the group Cr, Mo and W,
and X is a halogen from the group of Br, Cl and F.

The organic halide has an aryl ring, and therefore will react with molybdenum hexacarbonyl as in Step 1, or if desired, the active form of the catalyst may be prepared separately and added to the monomeric halide R-R'-X as in Step 2 where the halogen is removed resulting in the formation of a highly reactive carbonium ion, R-R$^{+'}$, which subsequently attacks the organic halide as in Step 3, with concurrent release of a hydrogen ion. The catalyst is again regenerated as by Step 4.

The reaction generally proceeds with substantial conversion of the monomer to the dimer R-R'-R-R'-X; then loss of the halogen again results in a carbonium ion which combines in a repetitive process to produce a polymer having an average number molecular weight ranging from approximately 5,000 to 30,000. Owing to the reactive sites of a phenyl ring, $o$, $m$, and $p$, to the ligand R', the polymer is highly branched.

Polymerization to form a linear copolymer according to the present invention is thought to proceed according to the following reaction mechanism:

Step 1

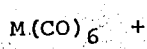 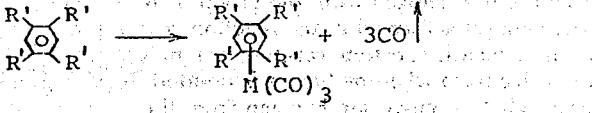

Step 2

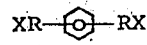 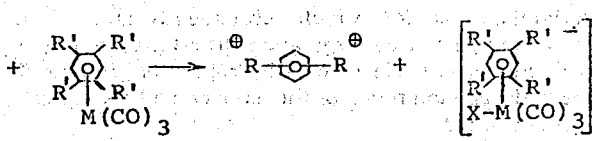

Step 3

 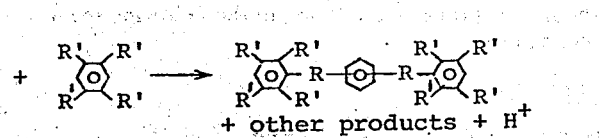

Step 4

 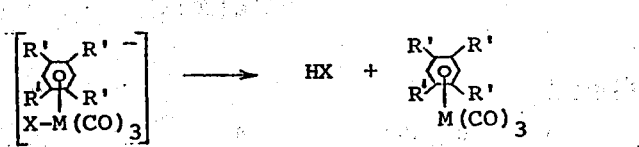

F(7)

where
R' is alkyl, alkoxide, or hydroxide as noted above
and R is alkyl, alkoxide, aldehyde, sulfonyl or haloalkyl as noted above,
and M is a metal from the group Cr, Mo and W,
and X is a halogen from the group of Br, Cl and F.

Removal of both halides from the dihalo-cmpound produces two reactive carbonium ions which will combine with the available positions of the aromatic substrate compound in a repetitive process to form a linear copolymer of average number molecular weight ranging between 5,000 and 30,000.

A sulfonylation according to the present invention is thought to proceed according to the following reaction mechanism:

Step 1

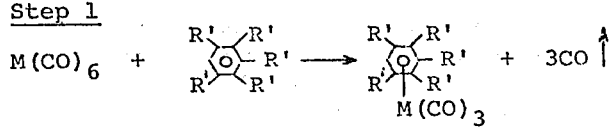

Step 2

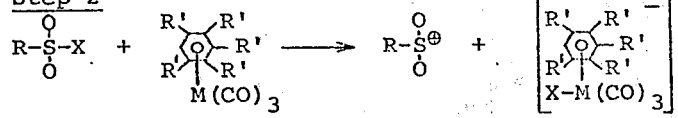

Step 3

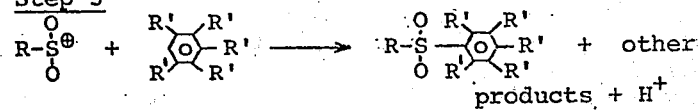

Step 4

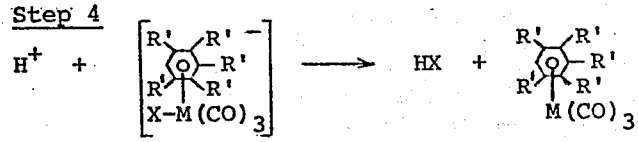

F(8)

where
R is an alkyl or alkyl substituted phenyl group as noted above
and R' is hydrogen, alkyl, alkoxide, aryl, aryloxide or hydroxide as noted above
and M is a metal from the group Cr, Mo and W,
and X is a halogen from the group of Br, Cl and F.

The catalyst is again formed in Step 1, as described before or merely added directly to the reactants. In Step 2 it proceeds to remove the halogen from sulfonyl halide, R-$SO_2$-X, resulting in the formation of a highly reactive sulfonium ion, R-$SO^+_2$, which subsequently attacks the aromatic substrate reactant as in Step 3, with concurrent release of a hydrogen ion. In Step 4, the hydrogen ion removes the halogen and the catalyst is regenerated.

A dehydrohalogenation according to the present invention is thought to proceed according to the following reaction mechanism:

where
R is an alkyl group as noted above
and R' is hydrogen, alkyl, alkoxide, sulfonyl chloride, amino, aryl and aryloxide, halide, hydroxide and alkylbenzoate esters as noted above
and M is a metal from the group Cr, Mo and W,
and X is a halogen from the group of Br, Cl and F.

In this reaction it is desirable to form the active catalyst apart from the reactants since M(CO)$_6$ will not combine with an alkyl halide and if an aryl halide is present some alkylation will occur. In Step 1, the catalyst removes the halogen from the alkyl halide, R-X, resulting in the formation of a highly reactive carbonium ion, R+. With subsequent loss of a hydrogen ion, as in Step 2, an alkene product is formed. In Step 3, the hydrogen ion removes the halogen and the catalyst is regenerated.

The invention will be more fully understood by reference to the following examples which describe the various types of reactions.

Step 1

Step 2

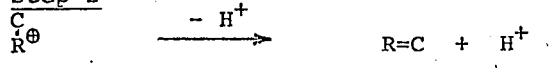

Step 3

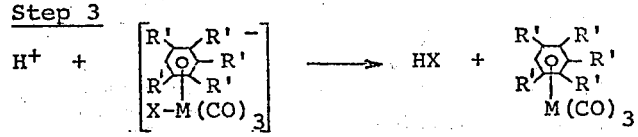

F(9)

EXAMPLE I

An alkylation by an organic halide of an aryl compound is promoted by the combination of 12.2 gms. of phenol; 20 cc. of t-butyl chloride; and 50 mg. of molybdenum hexacarbonyl in 120 cc. of the solvent heptane. These reactants are placed in a suitable vessel and mixed as by a magnetic stirring apparatus. The vessel is fitted with a reflux condenser and is then heated, to approximately 98° C. for 18 to 24 hours. At the end of this time period, the desired product is separated by suitable means well known to one skilled in the art.

EXAMPLE II

An acylation by an acid halide of an aryl compound is promoted by the combination of 125 cc. of anisole; 4 cc. of acetyl chloride and 25–50 mg. of molybdenum hexacarbonyl. These reactants are placed in a suitable vessel, and thoroughly mixed while refluxing at approximately 100° C. for 36 hours. At the end of this time period, the desired product is separated by suitable means.

EXAMPLE III

A polymerization of an organic halide to form a branched polymer is promoted by the combination of 100 gms. of benzyl chloride with 50 mg. of molybdenum hexacarbonyl. The compounds are placed in a suitable vessel, mixed and refluxed at approximately 100° C. for 1 hour. At the end of this time period, the branched polymer is separated by suitable means.

EXAMPLE IV

A linear polymer may be formed by combining 7.3 gms. of a,a' dichloro-p-xylene; 5.4 gms. of durene, and 10 mg. of molybdenum hexacarbonyl in 100 cc. of the solvent, decalin. The reactants are placed in a suitable vessel, mixed and refluxed at approximately 125°–130° C. for 3 hours. At the end of this time period the linear polymer is separated by suitable means.

EXAMPLE V

A sulfonylation of an aryl sulfonyl halide is promoted by combining 160 cc. of toluene; 3.8 gms. of p-tosyl chloride and 25 to 50 mg. of molybdenum hexacarbonyl in a suitable vessel. The reactants are then mixed and refluxed at approximately 110° C. for 36 hours. At the end of this time period, the desired product is separated by suitable means.

EXAMPLE VI

A dehydrohalogenation of an organic halide is promoted by the combination of 100 cc. of t-butyl chloride with 200 mg. of toluene molybdenum tricarbonyl. The compounds are placed in a suitable vessel, mixed and refluxed at approximately 51° C. for 4 hours. At the end of this time period the desired product is separated by suitable means.

The results of these and similar reactions have been set forth in Tables 1–5 below. In Table 1, examples 1–10 represent alkylations. In Table 2, examples 1–6 represent acylations. In Table 3, example 1 represents formation of a linear polymer and examples 2–3 represent formation of branched polymers and 4–5 represent branched or linear polymers. In Table 4, examples 1–3 represent sulfonylations. In Table 5, example 1, a dehydrohalogenation reaction was attempted without the arene metal tricarbonyl catalyst and no reaction was evidenced. In example 2, the catalyst was present, being first prepared as in F(2) above, and the alkene isobutylene, was quickly formed thereby. Although the product may be isolated, by continuing the reaction, the polymeric products which are known to occur when isobutyl cations attack isobutylene are prepared.

Thus, it can be seen that the disclosed invention carries out the object of the invention set forth above. As will be apparent to those skilled in the art, many modifications can be made without departing from the spirit of the invention herein disclosed and described, the scope of the invention being limited solely by the scope of the attached claims.

Table 1

| | Aromatic Substrate | Organic Halide | Alkylation Reactions Added Catalyst | Reaction Conditions | Yield | Comments |
|---|---|---|---|---|---|---|
| 1. | Toluene (100 ml) | t-butyl chloride (12.6 g) | Mo(CO)$_6$ (0.20 g) | Reflux 5 hr | 17.9 g 88% | Exclusively para substitution |
| 2. | Toluene (100 ml) | t-butyl chloride (12.6 g) | TolMo(CO)$_3$ (0.20 g) | Reflux 1 hr | 16.7 g 81.8% | |
| 3. | Toluene (160 ml) | Cyclohexyl chloride (10 g) | Mo(CO)$_6$ (0.05 g) | Reflux 6 hr | 19.7 g 84.5% | |
| 4. | Toluene (200 ml) | Benzyl chloride (12.6 g) | Mo(CO)$_6$ (0.03 g) | Reflux 12 hr | 16.4 g 90% | 100% alkylation, 10% polymer, 90% totyl-phenylmethane |
| 5. | Toluene (50 ml) | n-propyl chloride (8.9 g) | TolMo(CO)$_3$ (0.20 g) | 130° 6 hr | 7.8 g 50.5% | Carried out in glass-lined Parr bomb, product exclusively p-cymene |
| 6. | t-butyl benzene (55 ml) | n-chloroheptane (8.8 g) | Mo(CO)$_6$ (0.01 g) | 140° 24 hr | | Only secondary alkylates obtained |
| 7. | Toluene (75 ml) | Cyclohexyl fluoride (11.2 g) | TolMo(CO)$_3$ (0.1 g) | Reflux 6 hr | 12.8 g 67.3% | |
| 8. | Toluene (80 ml) | Cyclohexyl bromide (26.4 g) | TolMo(CO)$_3$ (0.1 g) | Reflux 8 hr | 6.7 g 23.4% | Extensive catalyst decomposition |
| 9. | Anisole (150 ml) | t-butyl chloride (6.8 g) | Mo(CO)$_6$ 0.03 g | 135° 24 hr | 9.5 g 79% | |
| 10. | Phenol | t-butyl chloride (12.0 g) | Mo(CO)$_6$ (0.01 g) | Reflux 18 hr | 18.8 g 96% | 120 ml heptane solvent. 93% p-t-butylphenol, 3% 2,6-di-t-butylphenol |

Table 2

Acylation Reactions

| | Aromatic Substrate | Organic Halide | Added Catalyst | Reaction Conditions | Yield | Comments |
|---|---|---|---|---|---|---|
| 1. | Toluene (100 ml) | Acetyl chloride (7.8 g) | $Mo(CO)_6$ (0.15 g) | Reflux 24 hr | 1.2 g 9% | Only p-methyl acetophenone isolated |
| 2. | Toluene (160 ml) | Propionyl chloride 6.35 g | $Mo(CO)_6$ (0.05 g) | Reflux 24 hr | 1.85 g 18% | Only para acylation obtained |
| 3. | Toluene (160 ml) | Benzoyl chloride 6.05 g | $Mo(CO)_6$ (0.15 g) | Reflux 18 hr | 2.5 g 29.7% | Only p-methyl benzophenone isolated |
| 4. | Toluene (160 ml) | Benzoyl chloride 6.05 g | $TolMo(CO)_3$ (0.02 g) | Reflux 12 hr | 5.65 g 67% | Same product as 3 |
| 5. | Anisole (125 ml) | Acetyl chloride 7.8 g | $Mo(CO)_6$ (0.02 g) | 100° 36 hr | 10.2 g 68% | 90% p-methoxyacetophenone, 4% o-methoxyacetophenone |
| 6. | Anisole (150 ml) | Benzoyl chloride (7.0 g) | $TolMo(CO)_3$ (0.15 g) | 100° 18 hr | 7.4 g 70% | Only p-methoxybenzophenone isolated |

Table 3

Polymerization Reactions

| | Aromatic Substrate | Organic Halide | Added Catalyst | Reaction Conditions | Yield | Comments |
|---|---|---|---|---|---|---|
| 1. | Durene | p-xylylene-dichloride | $Mo(CO)_6$ 0.01 g | 110° 3 hr | 9.6 g (98%) | Copolymer nearly insoluble in common organic solvents |
| 2. | Benzyl chloride (neat) | | $Mo(CO)_6$ (0.1 g) | 110° 1 hr | 100% | |
| 3. | Benzyl fluoride (neat) | | $TolMo(CO)_3$ | 140° | 100% | |
| 4. | Diphenyl ether (2.6 g) | Benzene-1,3-disulfonylchloride (4.3 g) | $Mo(CO)_6$ (0.1 g) | 110° 3 hr | 1.4 g 22% | Tan-colored copolymer |
| 5. | Diphenyl ether (2.6 g) | Benzene-1,3-disulfonylchloride (4.3 g) | $TolMo(CO)_3$ (0.1 g) | 110° 3 hr | 2.1 g 32% | Same as 4. |

Table 4

Sulfonylation Reactions

| | Aromatic Substrate | Organic Halide | Added Catalyst | Reaction Conditions | Yield | Comments |
|---|---|---|---|---|---|---|
| 1. | Toluene (160 ml) | Tosyl chloride (3.8 g) | $Mo(CO)_6$ (0.02 g) | Reflux 36 hr | 2.1 g 43% | Product is 4,4'-ditolylsulfone |
| 2. | Anisole (160 ml) | Tosyl chloride (3.8 g) | $Mo(CO)_6$ (0.02 g) | 135° 24 hr | 1.15 g 22% | Product is 4-methyl-4'-methoxydiphenylsulfone |
| 3. | Anisole (160 ml) | Tosyl chloride (3.8 g) | $TolMo(CO)_3$ (0.03 g) | 115° 18 hr | 1.3 g 25% | Same as 2 |

Table 5

Dehydrohalogenation Reaction

| | Aromatic Substrate | Organic Halide | Added Catalyst | Reaction Conditions | Yield | Comments |
|---|---|---|---|---|---|---|
| 1. | — | t-butyl chloride | $Mo(CO)_6$ | reflux, 20 hr. | none | no reaction, 96% $Mo(CO)_6$ recovered |
| 2. | — | t-butyl chloride (100 ml) | Toluene-$Mo(CO)_3$ (200 mg) | reflux, 4 hr. | — | large amounts of HCl evolved 2 polymeric substances obtained |

What is claimed is:

1. The process of reacting an organic halide with an aromatic substrate to form an aromatic product comprising the steps of: charging a reaction vessel with a metallic hexacarbonyl compound having the general formula $M(CO)_6$ wherein M is selected from the group consisting of Cr, Mo and W, adding an aromatic substrate having the general formula

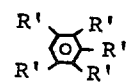

wherein R' is independently selected from the group consisting of hydrogen and hydroxide, with the proviso that at least one said R' is hydroxide, reacting said metallic hexacarbonyl compound with part of said aromatic substrate to yield an arene metal tricarbonyl catalyst having the general formula

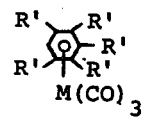

charging the reaction vessel with an organic halide having the general formula RX wherein R is selected from the group consisting of an alkyl group having from 1 to about 20 carbon atoms, a cyclohexyl and an alkyl substituted phenyl group having from 7 to about 12 carbon atoms, wherein the X constituent is attached to an alkyl carbon, and X is selected from the group consisting of bromine, chlorine and fluorine, heating said reaction vessel from ambient temperatures to a temperature sufficient to cause said catalyst to remove the halide from said organic halide with generation of a carbonium ion from said organic halide so that said carbonium ion will attack the remaining part of said aromatic substrate to yield the aromatic product.

2. The process as in claim 1, wherein said carbonium ion is formed in a temperature range from a few degrees above said ambient temperature to about 135° C.

3. The process as in claim 1, wherein said reaction is carried out in an inert atmosphere.

4. The process as in claim 3, wherein said inert atmosphere is nitrogen.

5. The process as in claim 1, wherein said reaction is carried out in a solvent selected from the group consisting of a saturated liquid hydrocarbon and liquid aryl compounds.

6. The process as in claim 1, wherein said organic halides are selected from the group consisting of n-propyl chloride, t-butyl chloride, cyclohexyl chloride, cyclohexyl fluoride, cyclohexyl bromide, n-chloroheptane and benzyl chloride.

7. The process as in claim 1, wherein said aromatic substrate is phenol.

8. The process as in claim 1, wherein the metal of said arene metal tri-carbonyl catalyst is molybdenum and where the R' constituent of said catalyst is selected from the group consisting of hydrogen and hydroxide radicals.

9. The process of reacting an organic halide in the presence of an arene metal tri-carbonyl catalyst with an aromatic substrate to form an aromatic product comprising the steps of: charging a reaction vessel with an organic halide having the general formula RX wherein R is selected from the group consisting of an alkyl group having from 1 to about 20 carbon atoms, a cyclohexyl and an alkyl substituted phenyl group having from 7 to about 12 carbon atoms, wherein the X constituent is attached to an alkyl carbon, and X is selected from the group consisting of bromine, chlorine and fluorine, adding an aromatic substrate having the general formula

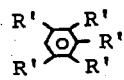

wherein R' is independently selected from the group consisting of hydrogen and hydroxide, with the proviso that at least one said R' is hydroxide, adding an arene metal tricarbonyl catalyst having the general formula

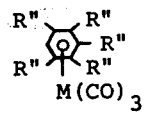

wherein R'' is independently selected from the group consisting of hydrogen, alkyl groups having from 1 to about 6 carbon atoms, alkoxide groups having from 1 to about 4 carbon atoms, aryl and aryloxide groups having from 6 to about 12 carbon atoms including alkyl substituents, amino, halide, alkyl benzoate esters having from 1 to 3 carbon atoms, sulfonyl chloride and hydroxide, and M is selected from the group consisting of Cr, Mo, and W, heating said reaction vessel from ambient temperatures to a temperature sufficient to cause said catalyst to remove the halide from said organic halide with generation of a carbonium ion from said organic halide so that said carbonium ion will attack said aromatic substrate to yield the aromatic product.

* * * * *